(12) United States Patent
Brandom et al.

(10) Patent No.: US 8,703,113 B2
(45) Date of Patent: Apr. 22, 2014

(54) SIDE-CHAIN CRYSTALLIZABLE POLYMERS FOR MEDICAL APPLICATIONS

(75) Inventors: Donald K. Brandom, Davis, CA (US); James E. McGrath, Blacksburg, VA (US); Joan Zeltinger, Encinitas, CA (US); Eric V. Schmid, San Diego, CA (US); Robert K. Schultz, Poway, CA (US)

(73) Assignee: REVA Medical Inc., San Diego, CA (US)

( * ) Notice: Subject to any disclaimer, the term of this patent is extended or adjusted under 35 U.S.C. 154(b) by 2785 days.

(21) Appl. No.: 11/335,771

(22) Filed: Jan. 18, 2006

(65) Prior Publication Data

US 2006/0182779 A1      Aug. 17, 2006

Related U.S. Application Data

(63) Continuation-in-part of application No. 11/176,638, filed on Jul. 7, 2005, now Pat. No. 7,939,611.

(60) Provisional application No. 60/586,796, filed on Jul. 8, 2004.

(51) Int. Cl.
    *A61K 31/74* (2006.01)
(52) U.S. Cl.
    USPC .................. 424/78.17; 424/78.08; 424/78.18; 424/78.31; 424/78.34; 424/78.37
(58) Field of Classification Search
    USPC ..................................................... 424/78.17
    See application file for complete search history.

(56) References Cited

U.S. PATENT DOCUMENTS

| | | | |
|---|---|---|---|
| 4,638,045 A | | 1/1987 | Kohn et al. |
| 4,863,735 A | | 9/1989 | Kohn et al. |
| 4,929,494 A | * | 5/1990 | Matsui et al. ................. 442/136 |
| 4,980,449 A | | 12/1990 | Kohn et al. |
| 5,163,952 A | * | 11/1992 | Froix ........................... 623/1.18 |
| 5,198,507 A | | 3/1993 | Kohn et al. |
| 5,443,477 A | | 8/1995 | Marin et al. |
| 5,466,439 A | | 11/1995 | Gibby et al. |
| 5,469,867 A | | 11/1995 | Schmitt |
| 5,670,602 A | | 9/1997 | Kohn et al. |
| 5,912,225 A | | 6/1999 | Mao et al. |
| 6,015,424 A | | 1/2000 | Rosenbluth et al. |
| 6,200,338 B1 | | 3/2001 | Solomon et al. |
| 6,238,687 B1 | | 5/2001 | Mao et al. |
| 6,375,669 B1 | | 4/2002 | Rosenbluth et al. |
| 6,388,043 B1 | | 5/2002 | Langer et al. |
| 6,475,477 B1 | | 11/2002 | Kohn et al. |
| 6,492,462 B2 | | 12/2002 | Bitler et al. |
| 6,544,453 B2 | | 4/2003 | Taft et al. |
| 6,550,480 B2 | | 4/2003 | Feldman et al. |
| 6,599,448 B1 | | 7/2003 | Ehrhard et al. |
| 6,623,521 B2 | | 9/2003 | Steinke et al. |
| 6,652,572 B2 | | 11/2003 | Kugler et al. |
| 6,831,116 B2 | | 12/2004 | Bitler et al. |
| 6,932,930 B2 | | 8/2005 | DeSimone et al. |
| 7,473,417 B2 | | 1/2009 | Zeltinger et al. |
| 2001/0046505 A1 | | 11/2001 | Kohn et al. |
| 2004/0086458 A1 | | 5/2004 | Kohn et al. |
| 2004/0086461 A1 | | 5/2004 | Kohn et al. |
| 2004/0127970 A1 | | 7/2004 | Saunders et al. |
| 2005/0106119 A1 | | 5/2005 | Brandom |

FOREIGN PATENT DOCUMENTS

| | | |
|---|---|---|
| GB | 1 244 207 | 8/1971 |
| JP | A-62-034101 | 2/1987 |
| JP | A-07-027766 | 1/1995 |
| JP | A-07-300555 | 11/1995 |
| JP | A-10-259298 | 9/1998 |
| WO | WO 98/20928 | 5/1998 |
| WO | WO 98/46286 | 10/1998 |
| WO | WO 99/24391 | 5/1999 |
| WO | WO 2004/110313 | 12/2004 |
| WO | WO 2006/014596 | 2/2006 |
| WO | WO 2006/020616 | 2/2006 |
| WO | WO98/36013 | 8/2008 |

OTHER PUBLICATIONS

Kong et al. Polymer(Korea) vol. 24. No. 2, pp. 141-148 (2000).*
Cretu et al. Polymer degradation and Stability, vol. 83, pp. 399-404 (2004).*
Kruft et al, "Studies on radio-opaque polymeric biomaterials with potential applications to endovascular prosthesesBiomaterials", 1996, 17, pp. 1803-1812).*
Hutmacher et al., "Scaffold-based tissue engineering: rationale for computer-aided design and solid free-form fabrication systems," Trends in Biotechnology vol. 22 No. 7, Jul. 2004, pp. 354-362.
Invitation to Pay Additional Fees in corresponding International application No. PCT/US2007/001011, mailed Mar. 4, 2008.
The International Search Report and the Written Opinion of the International Searching Authority in the PCT/US2007/081566. Mailing date: Aug. 28, 2008.
Benzina et al., "A versatile three-iodine molecular building block leading to new radiopaque polymeric biomaterials" Journal of Biomedical Materials Research, vol. 32, 459-466 (1996).
Translation to Japanese Office Action issued on Aug. 7, 2009 in the corresponding Japanese Application No. 2007-520544.

(Continued)

*Primary Examiner* — James Rogers
(74) *Attorney, Agent, or Firm* — Knobbe Martens Olson & Bear LLP

(57) ABSTRACT

Side-chain crystallizable (SCC) polymers are useful in various medical applications. In certain applications, heavy atom containing side-chain crystallizable polymers (HACSCCP's) are particularly useful. An example of a HACSCCP is a polymer that comprises a main chain, a plurality of crystallizable side chains, and a plurality of heavy atoms attached to the polymer. In certain configurations, the heavy atoms are present in an amount that is effective to render the polymer radiopaque. A polymeric material that includes an HAC-SCCP may be fabricated into a medical device useful for at least partially occluding a body cavity. For example, such a medical device may be an embolotherapy product. A polymeric material that includes a SCC polymer may also be fabricated into other medical devices, such as stents.

1 Claim, 1 Drawing Sheet

(56) References Cited

OTHER PUBLICATIONS

Aharoni, et al., "Rigid Backbone Polymers. 2. Polyisocyanates and Their Liquid-Crystal Behavior" *Macromolecules*, 12(1):94-1O3 (1979).

Andruzzi, et al., "Studies on Comb-like Polymers. 2. Poly(octadecylethylene oxide)" *Macromolecules*, 13:15-18(1980).

Cabasso, et al., "Radiopaque Miscible Systems Composed of Poly(Methyl Methacrylate) and Transition and Nontransition Metal Salts: Spectroscopic, Thermal, and Radiographic Characterization" *Journal of Applied Polymer Science*, 38:1653-1666 (1989).

Cabasso, et al., "Radiopaque Polymers Based on Acrylated Phosphonate Esters Derived from Polyols" *Journal of Applied Polymer Science*, 41:3025-3042(1990).

Chupov, et al., "Structure and Physico-Chemical Properties of Comb-Like Polypeptides Based on Poly-L-Lysine*" *Polymer Science U.S.S.R.* 21:241-252 (1979).

Gonzalez, et al. Side-Chain Crystallinity, Heat of Melting, and Thermal Transitions in poly[$N$-(10-n-Alkyloxycarbonyl-$n$-Decyl)Maleimides] (PEMI) *Journal of Polymer Science: Polymer Physics Edition*. 18:2197-2207 (1980).

Greenberg, et al., "Side Chain Crystallization of $n$-Alkyl Polymethacrylates and Polyacrylates" *Institute of Polymer Research, Polytechnic Institute of Brooklyn.* 76:6280-6285. (1954).

Hooper, et al., "Diphenolic monomers derived form the natural amino acid alpha-l-tyrosine: an evaluation of peptide coupling techniques" *Journal of Bioactive and Compatible Polymers*, 10(4):327-340 XP002045571, 1995.

Jayakrishnan, et al., "Synthesis and Polymerization of Some Iodine-Containing Monomers for Biomedical Applications" *Journal of Applied Polymer Science* 44:743-748 (1992).

Jordan, et al., "Side-Chain Crystallinity. I. Heats of Fusion and Melting Transitions on Selected Homopolymers Having Long Side Chains" *Journal of Polymer Science: Part A-1*, 9:1835-1852 (1971).

Jordan, et al., "Side-Chain Crystallinity. II. Heats of Fusion and Melting Transitions on Selected Copolymers Incorporating $n$-Octadecyl Acrylate or Vinyl Stearate" *Journal of Polymer Science:Part A-1*, 9:3349-3365 (1971).

Jordan, et al., "Side-Chain Crystallinity. III. Influence of Side-Chain Crystallinity on the Glass Transition Temperatures of Selected Copolymers Incorporating $n$-Octadeeyl Acrylate or Vinyl Stearate" *Journal of Polymer Science: Part A-1* 9:3367-3378(1971).

Jordan, et al., "Side-Chain Crystallinity. V. Heats of Fusion and Melting Temperatures on Monomers Whose Homopolymers Have Long Side Chains" *Journal of Polymer Science*, 10:3347-3366 (1972).

Kruft, et al., "In vivo tissue compatibility of two radio-opaque polymeric biomaterials" *Biomaterials*, 18:31-35(1997).

Kruft, et al., "Studies on radio-opaque polymeric biomaterials with potential applications to endovascular prostheses" *Biomaterials*, 17:1803-1812 (1996).

Magagnini, et al., "Studies on Comb-like Polymers. 1. Poly(octadecylethylene)" *Macromolecules*, 13:12-15(1980).

Mao, et al. "Synthesis and Biological Properties of Polymer Immunoadjuvants" *Polymer Journal*, 25(5):499-505 (1993).

O'Driscoll, et al., "Kinetics of Anionic Copolymerization of Monomers of Similar Polarities" *Journal of Polymer Science*, 61:19-24 (1962).

Overberger, et al., "The Preparation and Polymerization of $p$-Alkylstyrenes. Effect of Structure on the TransitionTemperatures of the Polymers" *The Department of Chemistry, Institute of Polymer Research, Polytechnic Institute of Brooklyn.* 75:3326-3330, 1953.

Pittman, et al., "Effect of Polymer Crystallinity on the Wetting Properties of Certain Fluroalkyl Acrylates" *Journal of Polymer Science Part A-1*, 7:3053-3066 (1969).

Plate, et al., "Comb-Like Polymers. Structure and Properties" *J. Polymer Sci.:Macromolecular Reviews*, 8:117-253(1974).

Pulapura et al. "Structure-Property Relationships for the Design of Polyiminocarbonates" *Biomaterials* 11(9):666-678. XP000172545, 1990.

Rabolt, et al., "Studies of Chain Conformational Kinetics in Poly(di-$n$-alkylsilanes) by Spectroscopic Methods. 1.Poly(di-$n$-hexylsilane), Poly(di-$n$-heptylsaline), and Poly(di-$n$-octylsilane)." *Macromolecules*, 19:611-616 (1986).

Wada, et al., "Effect of Amount of Medium on the Radiation-Induced Polymerization of Ethylene in *tert*-Butyl Alcohol" *Journal of Polymer Science: Part A-1*, 10:1655-1667 (1972).

Watanabe, et al., "Thermotropic Polypeptides. 2. Molecular Packing and Thermotropic Behavior of Poly (L-glutamates) with Long $n$-Alkyl Side Chains", *Macromolecules* 18:2141-2148 (1985).

International Search Report for Application No. PCT/US2005/024289 mailed Dec. 6, 2005.

International Search Report for Application No. PCT/US2005/028228 mailed Nov. 30, 2005.

U.S. Appl. No. 11/200,656, filed Aug. 10, 2005.

U.S. Appl. No. 11/176,638, filed Jul. 7, 2005.

* cited by examiner

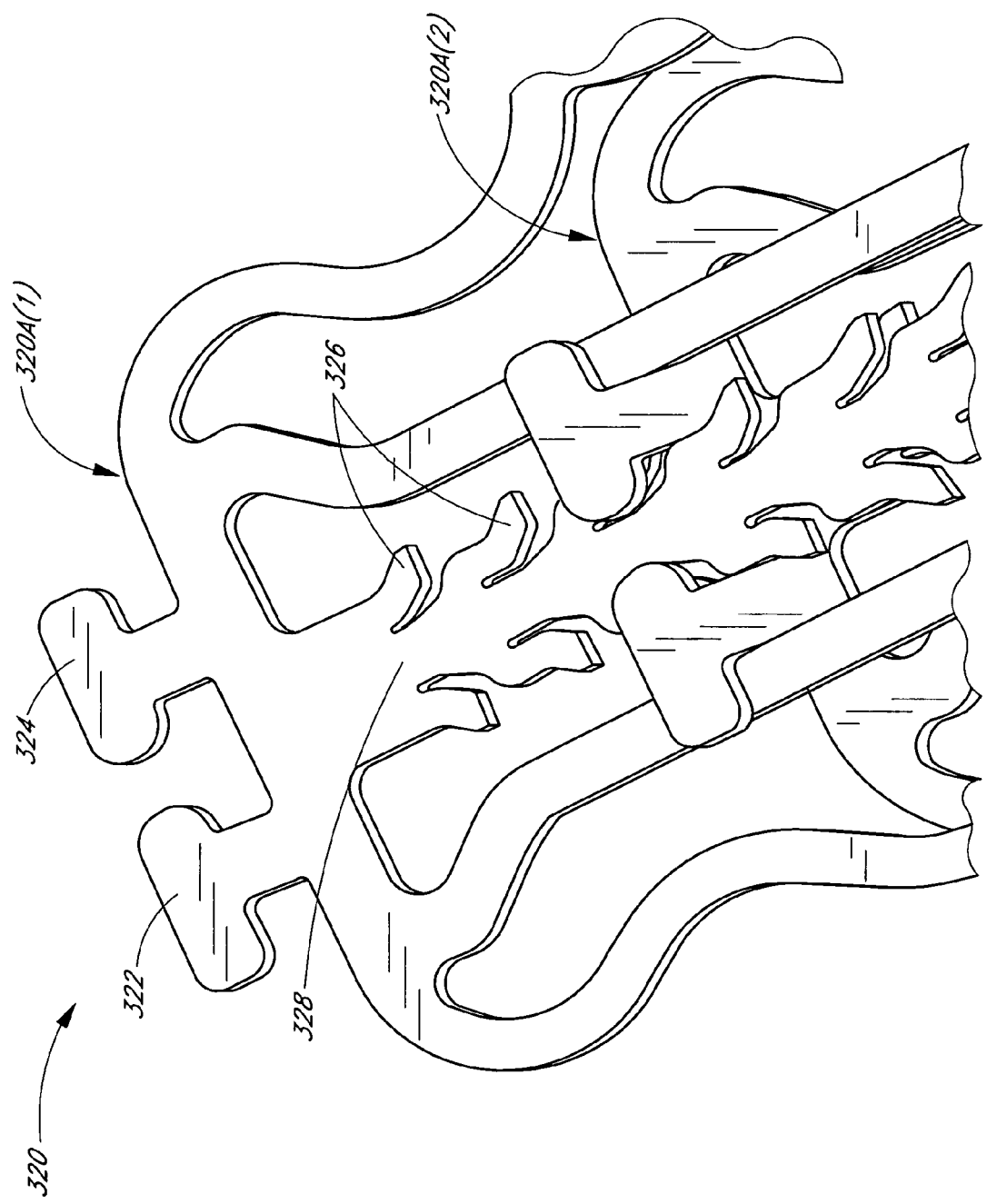

SIDE-CHAIN CRYSTALLIZABLE POLYMERS FOR MEDICAL APPLICATIONS

CROSS-REFERENCE TO RELATED APPLICATIONS

This application is a continuation-in part of U.S. patent application Ser. No. 11/176,638, filed Jul. 7, 2005 now U.S. Pat. No. 7,939,611, which claims priority to U.S. Provisional Patent Application No. 60/586,796, filed Jul. 8, 2004, both of which are hereby incorporated by reference in their entireties.

BACKGROUND

1. Field of the Invention

This invention relates to side-chain crystallizable polymers, and particularly to side-chain crystallizable polymers useful in medical applications.

2. Description of the Related Art

Polymeric materials are widely used in numerous applications. For example, therapeutic embolization is the selective blockage of blood vessels or diseased vascular structures. Examples of polymeric embolotherapy devices and reagents include embolic coils, gel foams, glues, and particulate polymeric embolic agents used, for example, to control bleeding, prevent blood loss prior to or during a surgical procedure, restrict or block blood supply to tumors and vascular malformations, e.g., for uterine fibroids, tumors (i.e., chemo-embolization), hemorrhage (e.g., during trauma with bleeding) and arteriovenous malformations, fistulas (e.g., AVF's) and aneurysms.

Polymeric liquid embolic agents include precipitative and reactive systems. For example, in a precipitative system, a polymer may be dissolved in a biologically acceptable solvent that dissipates upon vascular delivery, leaving the polymer to precipitate in situ. Reactive systems include cyanoacrylate systems in which, e.g., a liquid monomeric and/or oligomeric cyanoacrylate mixture is introduced to the vascular site through a catheter and polymerized in situ. In this system, polymerization is initiated by the available water in the blood.

A number of technological applications involve the use of a polymer that undergoes a transition upon a change in temperature. For example, in the medical field, one way to introduce a solid polymer into a particular body region is to heat the polymer into a flowable state, then inject the polymer into the region and allow it to cool and solidify. U.S. Pat. No. 5,469,867 discloses side-chain crystallizable polymers that are said to be useful for occluding channels in a living mammal. Such polymers are said to be designed such that they can be melted so that they are flowable slightly above body temperature but solidify when cooled to body temperature.

SUMMARY

An embodiment provides a polymer that includes a main chain, a plurality of cyrstallizable side chains, and a plurality of heavy atoms attached to the polymer. The heavy atoms may be present in an amount that is effective to render the polymer radiopaque. In an embodiment, the polymer comprises a recurring unit of the formula (VI) as set forth below. Another embodiment provides a medical device that comprises such a polymer.

Another embodiment provides a medical device that includes a polymeric material, the polymeric material comprising a biocompatible inherently radiopaque side chain crstallizable polymer. In an embodiment, the medical device comprises at least a stent.

Another embodiment provides a method of treatment that includes introducing a medical device into a body cavity of a mammal in an amount that is effective to at least partially occlude the body cavity, wherein the medical device comprises a polymeric material, and wherein the polymeric material comprises a side chain crystallizable polymer. In an embodiment, the method further includes forming a channel through the medical device.

Another embodiment provides a method for making an inherently radiopaque side chain crystallizable polymer, comprising copolymerizing a first monomer and a second monomer, the first monomer comprising a heavy atom and the second monomer comprising a crystallizable group.

Another embodiment provides a method for making an inherently radiopaque side chain crystallizable polymer, comprising reacting a side chain crystallizable polymer with a heavy metal reagent under conditions selected to attach a plurality of heavy atoms to the side chain crystallizable polymer.

Another embodiment provides a stent that comprises a side chain crystallizable polymer.

These and other embodiments are described in greater detail below.

BRIEF DESCRIPTION OF THE DRAWING

FIG. 1 is a detailed view of a slide-and-lock stent configuration in accordance with one preferred embodiment of the present invention, comprising deflectable teeth with deflect downward to provide a stent exhibiting mono-directional expansion.

DETAILED DESCRIPTION OF THE PREFERRED EMBODIMENTS

An embodiment provides a heavy atom-containing side-chain crystallizable polymer ("HACSCCP"). Many polymers contain relatively low atomic number atoms such as hydrogen, carbon, nitrogen, oxygen, silicon and sulfur. However, it has been found that the attachment of relatively higher atomic number atoms to the polymer may affect various physical and mechanical properties of the polymer. For example, attachment of heavy atoms to a polymer in sufficient amounts may advantageously render the polymer easier to detect by various medical imaging techniques. The term "heavy atom" is used herein to refer to atoms having an atomic number of 17 or greater. Preferred heavy atoms have an atomic number of 35 or greater, and include bromine, iodine, bismuth, gold, platinum tantalum, tungsten, and barium. In certain configurations, HACSCCP's may be inherently radiopaque. The term "inherently radiopaque" is used herein to refer to a polymer to which a sufficient number of heavy atoms are attached by covalent or ionic bonds to render the polymer easier to detect by medical imaging techniques (e.g., by X-rays and/or during fluoroscopy). HACSCCP's may be used in a variety of applications, including medical applications in which they are configured to provide a degree of inherent radiopacity that may provide significant advantages. It will be understood that the degree to which the attached heavy atoms render the polymer easier to detect by medical imaging techniques will generally depend on the amount of heavy atoms incorporated into the polymer and the configuration (e.g., thickness) of the polymer.

In addition to heavy atoms, HACSCCP's also contain crystallizable side chains. Side chain crystallizable (SCC) polymers, sometimes called "comb-like" polymers, are well-known, see N. A. Plate and V. P. Shibaev, J. Polymer Sci.: Macromol. Rev. 8:117-253 (1974), the disclosure of which is hereby incorporated by reference. It will be understood that HACSCCP's are a type of SCC polymer, and that reference herein to SCC polymers includes HACSCCP's, unless otherwise stated. In an embodiment, the SCC polymer is substantially free of heavy atoms. HACSCCP's may be SCC polymers that have been modified to include heavy atoms, e.g., by bonding heavy atoms to an SCC polymer and/or by making a HACSCCP by polymerizing monomers that contain heavy atoms. SCC polymers may have various configurations, e.g., homopolymer, copolymer (e.g., random copolymer, alternating copolymer, block copolymer, graft copolymer), various tacticities (e.g., random, isotactic, atactic, syndiotactic), etc. A SCC polymer may be a mixture or blend of two or more SCC polymers, each of the individual SCC polymers in the mixture or blend having different configurations, different levels of heavy atom content, molecular weights, melting points, etc. The polymer backbone or main chain of the SCC polymer, to which the crystallizable side chains are attached, may be configured in various ways, e.g., linear, branched, crosslinked, dendritic, single-stranded, double-stranded, etc. Preferred SCC polymers for medical applications are inherently radiopaque, biocompatible and/or bioresorbable. The heavy atoms may be attached to the main chain and/or the side chains of a HACSCCP.

The crystallizable side chains of SCC polymers (including, e.g., HACSCCP's) are preferably selected to crystallize with one another to form crystalline regions and may comprise, for example, $-(CH_2)_n-$ and/or $-((CH_2)_m-O-)_n$ groups. The side chains are preferably linear to facilitate crystallization. For SCC polymers that contain $-(CH_2)_n-$ groups in the crystallizable side chain, n is preferably in the range of about 6 to about 30, more preferably in the range of about 20 to about 30. For SCC polymers that contain $-((CH_2)_m-O-)_n$ groups in the crystallizable side chain, n is preferably in the range of about 6 to about 30 and m is preferably in the range of about 1 to about 8. More preferably, m and n are selected so that the $((CH_2)_m-O-)_n$ groups contain from about 6 to about 30 carbon atoms, even more preferably from about 20 to about 30 carbon atoms. The spacing between side chains and the length and type of side chain are preferably selected to provide the resulting SCC polymer with a desired melting point. For example, for medical applications (e.g., embolotherapy), the spacing between side chains and the length and type of the side chains are preferably selected to provide the SCC polymer (and/or the material into which it is incorporated) with a melting point in the range of about 30° C. to about 80° C. As the spacing between side chains increases, the tendency for the side chains to be crystallizable tends to decrease. Likewise, as the flexibility of the side chains increases, the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains of the SCC polymer.

Examples of SCC polymers include versions of the following polymers that are selected so that the alkyl group is sufficiently long (e.g., greater than about 6 carbons) to provide the desired melting point and, for HACSCCP's, modified to include heavy atoms, e.g., sufficient heavy atoms to render them radiopaque: poly(1-alkene)s, poly(alkyl acrylate)s, poly(alkyl methacrylate)s, poly(alkyl vinyl ether)s, and poly(alkyl styrene)s. Examples of SCC polymers further include versions of the polymers disclosed in the following references that include (or have been modified to include) crystallizable side chains and, for HACSCCP's, heavy atoms, e.g., sufficient heavy atoms to render them radiopaque: U.S. Pat. Nos. 4,638,045; 4,863,735; 5,198,507; 5,469,867; 5,912,225; and 6,238,687; as well as U.S. Provisional Patent Application No. 60/601,526, filed 13 Aug. 2004; all of which are incorporated by reference in their entireties, and particularly for the purpose of describing SCC polymers and methods for making them.

In an embodiment, the side chains are selected to provide the SCC polymer (or material into which the SCC polymer is incorporated) with a controllable melting temperature. In a preferred embodiment, polymeric embolotherapy products include HACSCCP's configured to render the embolotherapy product detectable by a technique such as X-ray. The side chains of the included HACSCCP may be selected so that the polymeric embolotherapy product has a melting point higher than the body temperature of the mammal for which the product is intended. Such a polymeric embolotherapy product may, for example, be heated above the melting temperature to render it more flowable, thereby facilitating delivery to the target vasculature, where it may cool and solidify to embolize the vasculature. The use of inherently radiopaque HACSCCP's to provide radiopacity and a controlled melting point may be particularly advantageous in medical applications, but those skilled in the art will recognize additional applications as well. Thus, while the various descriptions herein regarding the use of SCC polymers may indicate a preference for medical applications, it will be understood that various technologies outside the medical area may also benefit from the use of SCC polymers, and particularly HACSCCP's.

Furthermore, in some embodiments, the present SCC polymers may be used to develop various medical devices. For instance, pre-fabricated off-the-shelf devices, rapidly prototyped devices, real-time prototype devices using computer technology. Additionally present polymers may be delivered directly to a non-lumen or non-cavity of the body. The various medical devices may include but are not limited to stents and stent grafts for vascular and body lumen applications, pins, screws, sutures, anchors and plates for reconstructive skeletal or soft tissue applications, cartilage replacements. SCC polymers may be placed directly in body tissue for example in subcutaneous and intramuscular tissue.

An embodiment of a HACSCCP is a polymer comprising a main chain, a plurality of crystallizable side chains, and a plurality of heavy atoms attached to the polymer, the heavy atoms being present in an amount that is effective to render the polymer radiopaque. A polymer that comprises a recurring unit of the formula (I) is an example of such an HACSCCP:

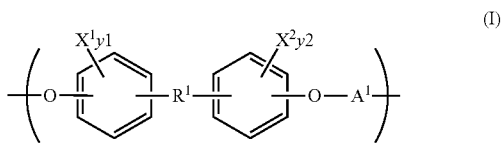

(I)

In formula (I), $X^1$ and $X^2$ are each independently selected from the group consisting of Br and I; $y^1$ and $y^2$ are each independently zero or an integer in the range of 1 to 4; and $A^1$ is selected from the group consisting of

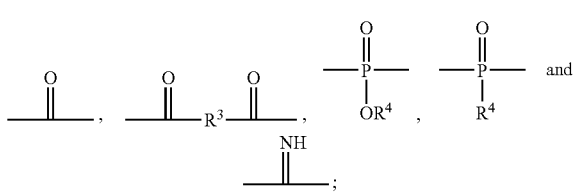

$R^3$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl; $R^4$ selected from the group consisting of H, $C_1$-$C_{30}$ alkyl, and $C_1$-$C_{30}$ heteroalkyl; $R^1$ is

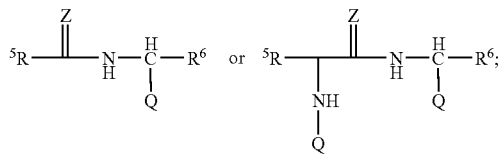

$R^5$ and $R^6$ are each independently selected from the group consisting of —CH=CH—, —CHJ$^1$-CHJ$^2$-, and —(CH$_2$)$_a$—; a is zero or an integer in the range of 1 to 8; $J^1$ and $J^2$ are each independently selected from the group consisting of Br and I; and Z is an O or an S; and Q is a crystallizable group comprising from about 6 to about 30 carbon atoms, preferably from about 20 to about 30 carbon atoms. In an embodiment, Q is:

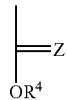

Polymers of the formula (I) may be prepared by modifying the general methods described in U.S. Provisional Patent Application No. 60/601,526, filed 13 Aug. 2004, to select the appropriate side chain length, side chain spacing and halogen content.

It will be recognized that Q and/or $R^4$ may comprise crystallizable side chains, that each of X, $J^1$ and $J^2$ is a heavy atom, and that y may be adjusted so that the number of heavy atoms in the polymer is sufficient to render the polymer radiopaque. Q and $R^4$ may each independently comprise units selected from the group consisting of —(CH$_2$)$_{n1}$— and —((CH$_2$)$_{m1}$—O—)$_{n1}$; where m1 and n1 are each independently selected so that Q and/or $R^4$ each independently contain from about 1 to about 30 carbon atoms, preferably from about 6 to about 30 carbon atoms, and more preferably from about 20 to 30 carbon atoms. Moreover, Q and $R^4$ may include other functional groups such as ester and amide, and/or heavy atoms such as iodine and bromine. Non-limiting examples of Q and $R^4$ thus include —$C_{n1}H_{2n1+1}$, —CO$_2$—$C_{n1}H_{2n1+1}$, —CONH—$C_{n1}H_{2n1+1}$, —(CH$_2$)$_{n1}$—Br, —(CH$_2$)$_{n1}$—I, —CO$_2$—(CH$_2$)$_{n1}$—Br, —CO$_2$—(CH$_2$)$_{n1}$—I, —CONH—CO$_2$—(CH$_2$)$_{n1}$—Br, and —CONH—CO$_2$—(CH$_2$)$_{n1}$—I. In an embodiment, $R^5$ is —CH=CH— or —(CH$_2$)$_a$—; $R^6$ is —(CH$_2$)$_a$—; and Q is an ester group comprising from about 10 to about 30 carbon atoms.

It will be understood that a polymer that comprises a recurring unit of the formula (I) may be a copolymer, e.g., a polymer of the formula (I) that further comprises recurring —$R^2$-$A^2$- units, where $R^2$ is selected from the group consisting of —(CH$_2$)$_{n2}$— and —((CH$_2$)$_{m2}$—O—)$_{n2}$; where m2 and n2 are each independently selected so that $R^2$ contains from about 1 to about 30 carbon atoms; and where $A^2$ is defined in the same manner as $A^1$ above. Thus, an embodiment provides a polymer comprising recurring units of the formula (Ia):

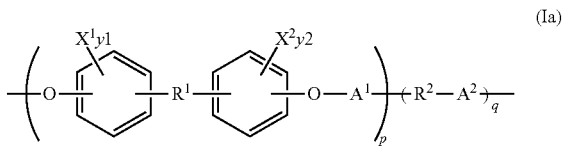

In formula (Ia), $X^1$, $X^2$, $y^1$, $y^2$, $R^1$ and $A^1$ are defined as described above for formula (I); p and q may each be independently varied over a broad range to provide a polymer having the desired properties, e.g., melting point, radiopacity, and viscosity, using routine experimentation. In an embodiment, p and q are each independently an integer in the range of 1 to about 10,000. It will be appreciated that the formula (I) units and —($R^2$-$A^2$)— units in a polymer comprising recurring units of the formula (Ia) may be arranged in various ways, e.g., in the form of a block copolymer, random copolymer, alternating copolymer, etc.

Another embodiment of a HACSCCP (e.g., a polymer comprising a main chain, a plurality of crystallizable side chains, and a plurality of heavy atoms attached to the polymer, the heavy atoms being present in an amount that is effective to render the polymer radiopaque) comprises a recurring unit of the formula (II):

In formula (II), $R^7$ is H or CH$_3$; $A^3$ is a chemical group having a molecular weight of about 500 or less; and $A^3$ bears at least one of the heavy atoms attached to the polymer. Non-limiting examples of $A^3$ include metal carboxylate (e.g., —CO$_2$Cs), metal sulfonate (e.g., —SO$_4$Ba), halogenated alkyl ester (e.g., —CO$_2$—(CH$_2$)$_b$—Br), halogenated alkyl amide (e.g., —CONH—(CH$_2$)$_b$—Br), and halogenated aromatic (e.g., —C$_6$H$_4$—I), where b is an integer in the range of about 1 to about 4. In an embodiment, $A^3$ comprises an aromatic group bearing at least one halogen atom selected from the group consisting of bromine and iodine. In another embodiment, $A^3$ comprises a chemical group of the formula -L$_1$-(CH$_2$)$_{n3}$-L$_2$-Ar$^1$, wherein L$_1$ and L$_2$ each independently represent a nullity (i.e., are not present), ester, ether or amide group; n3 is zero or an integer in the range of about 1 to about 30; and Ar$^1$ comprises a halogenated aromatic group containing from about 2 to about 20 carbon atoms. HACSCCP's that comprise a recurring unit of the formula (II) may be formed by polymerization of the corresponding monomers or by post-reaction of appropriate polymeric precursors. HACSCCP's that comprise a recurring unit of the formula (II) may be copolymers that include additional recurring units.

Side chain $A^3$ groups in a HACSCCP comprising a recurring unit of the formula (II) may be crystallizable and/or the HACSCCP comprising a recurring unit of the formula (II) may further comprise a second recurring unit that comprises a crystallizable side chain. Examples of suitable second recurring units having crystallizable side chains include the following: poly(1-alkene)s, poly(alkyl acrylate)s, poly(alkyl methacrylate)s, poly(alkyl vinyl ether)s, and poly(alkyl styrene)s. The alkyl groups of the foregoing exemplary second recurring units preferably contain more than 6 carbon atoms, and more preferably contain from about 6 to about 30 carbon atoms. For example, in an embodiment, the second recurring unit is of the formula (III):

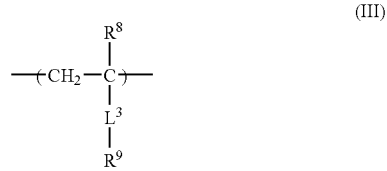

(III)

In formula (III), $R^8$ is H or $CH_3$; $L^3$ is an ester or amide linkage; and $R^9$ comprises a $C_6$ to $C_{30}$ hydrocarbon group. HACSCCP's comprising a recurring unit of the formula (II) and a second recurring unit (such as a recurring unit of the formula (III)) may be formed by copolymerization of the corresponding monomers and/or by post-reaction of appropriate polymeric precursors.

Another embodiment of a HACSCCP (e.g., a polymer comprising a main chain, a plurality of crystallizable side chains, and a plurality of heavy atoms attached to the polymer, the heavy atoms being present in an amount that is effective to render the polymer radiopaque) comprises a recurring unit of the formula (IV), where $A^3$ is defined above:

(IV)

In formula (IV), $A^4$ represents H or a group containing from about 1 to about 30 carbons, e.g., a $C_1$-$C_{30}$ hydrocarbon. Side chain $A^3$ and/or $A^4$ groups in a HACSCCP comprising a recurring unit of the formula (IV) may be crystallizable and/or the HACSCCP comprising a recurring unit of the formula (IV) may further comprise a second recurring unit that comprises a crystallizable side chain. For example, in an embodiment, the second recurring unit is of the formula (V), where $R^{10}$ comprises a $C_6$ to $C_{30}$ hydrocarbon group and $R^{11}$ represents H or a group containing from about 1 to about 30 carbons, e.g., a $C_1$-$C_{30}$ hydrocarbon:

(V)

Another embodiment of a HACSCCP comprises a recurring unit of the formula (VI):

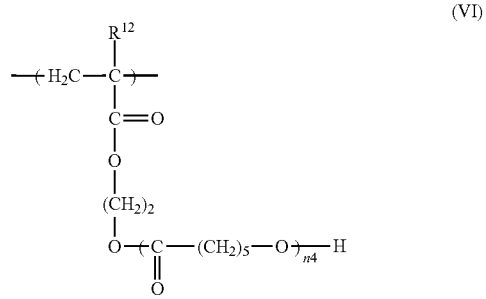

(VI)

wherein $R^{12}$ is H or $CH_3$ and n4 is an integer in the range of about 1 to about 1,000. In preferred embodiments, a HACSCCP comprising a recurring unit of the formula (VI) is biocompatible. In another embodiment, a medical device (e.g., a stent, catheter or any other medical device described herein) comprises a polymer that comprises a recurring unit of the formula (VI). Recurring units of the formula (VI) may be formed in various ways. For example, a starting polymer comprising recurring hydroxyethylmethacrylate (HEMA) units may be provided, and at least a portion of those recurring hydroxyethylmethacrylate (HEMA) units may be reacted with caprolactone to form recurring units of the formula (VIa) having crystallizable poly(caprolactone) (PCL) groups in the side chain as illustrated in Scheme A below.

Scheme A

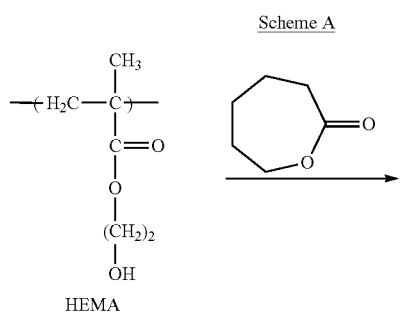

HEMA

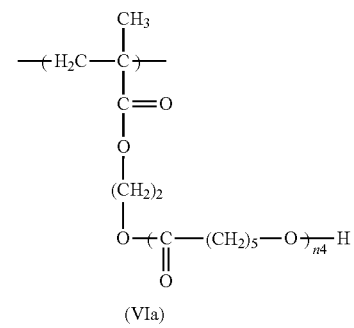

(VIa)

Polymerization of the caprolactone to form the crystallizable PCL groups may be conducted by using an appropriate catalyst, e.g., stannous octoate. The melting point of the side chain (and the HACSCCP) may be controlled by manipulating the degree of polymerization (n4) of the PCL groups, e.g., by adjusting the relative amounts of HEMA recurring units and caprolactone monomer during polymerization, in a manner generally know to those skilled in the art. The melting point may also be controlled by manipulating the spacing along the polymer backbone between PCL groups, e.g., by appropriate selection of the amount of HEMA recurring units in the starting polymer. In an embodiment, n4 is an integer in the range of about 2 to about 10. Heavy atoms may be included in a HACSCCP that comprises a recurring unit of the formula (VI) in various ways, e.g., the HACSCCP may further comprise a recurring unit of the formula (II) as described above.

SCC polymers are not limited to those described above (e.g., not limited to HACSCCP's comprising recurring units of the formulae (I) to (VI)), and further include versions of known polymers that have been modified to include side-chain crystallizable groups and/or sufficient heavy atoms to render the resulting polymer radiopaque. Those skilled in the art will understand that HACSCCP's may be prepared in various ways, e.g., by employing routine experimentation to modify known methods for making SCC polymers to thereby incorporate heavy atoms into the resulting polymers. For example, inherently radiopaque versions of the side chain crystallizable polymers described in U.S. Pat. No. 5,469,867 may be prepared by copolymerizing the corresponding monomers with monomers that contain heavy atoms. U.S. Pat. No. 5,469,867 is incorporated by reference and particularly for the purpose of describing monomers, polymers and methods of polymerization. Examples of suitable monomers that contain heavy atoms are disclosed in Kruft, et al., "Studies On Radio-opaque Polymeric Biomaterials With Potential Applications To Endovascular Prostheses," Biomaterials 17 (1996) 1803-1812; and Jayakrishnan et al., "Synthesis and Polymerization of Some Iodine-Containing Monomers for Biomedical Applications," J. Appl. Polm. Sci., 44 (1992) 743-748. HACSCCP's may also be prepared by post-reaction, e.g., by attaching heavy atoms to the polymers described in U.S. Pat. No. 5,469,867. Specific examples of SCC polymers that may be modified with heavy atoms to make HACSCCP's include the acrylate, fluoroacrylate, methacrylate and vinyl ester polymers described in J. Poly. Sci., 10.3347 (1972); J. Poly. Sci. 10:1657 (1972); J. Poly. Sci. 9:3367 (1971); J. Poly. Sci. 9:3349 (1971); J. Poly. Sci. 9:1835 (1971); J.A.C.S. 76:6280 (1954); J. Poly. Sci. 7:3053 (1969); Polymer J. 17:991 (1985), corresponding acrylamides, substituted acrylamide and maleimide polymers (J. Poly. Sci.: Poly. Physics Ed. 11:2197 (1980); polyolefin polymers such as those described in J. Poly. Sci.: Macromol. Rev. 8:117-253 (1974) and Macromolecules 13:12 (1980), polyalkyl vinylethers, polyalkylethylene oxides such as those described in Macromolecules 13:15 (1980), alkylphosphazene polymers, polyamino acids such as those described in Poly. Sci. USSR 21:241, Macromolecules 18:2141, polyisocyanates such as those described in Macromolecules 12:94 (1979), polyurethanes made by reacting amine- or alcohol-containing monomers with long-chain alkyl isocyanates, polyesters and polyethers, polysiloxanes and polysilanes such as those described in Macromolecules 19:611 (1986), and p-alkylstyrene polymers such as those described in J.A.C.S. 75:3326 (1953) and J. Poly. Sci. 60:19 (1962). The foregoing SCC polymers may be modified with heavy atoms to make HACSCCP's in various ways. For example, monomers bearing heavy atoms may be prepared by iodinating and/or brominating the monomers used to make the foregoing polymers. Those heavy atom-bearing monomers may then be copolymerized with the unmodified monomers to prepare HACSCCP's. Those skilled in the art may identify conditions for making the heavy atom-bearing monomers and corresponding HACSCCP's by routine experimentation.

In another embodiment, a HACSCCP is prepared by reacting a side chain crystallizable polymer with a heavy metal reagent under conditions selected to attach a plurality of heavy atoms to the side chain crystallizable polymer. For example, the side chain crystallizable polymer may be exposed to a heavy metal reagent that comprises bromine and/or iodine. Examples of heavy metal reagents include bromine vapor, iodine vapor, bromine solution and iodine solution. The side chain crystallizable polymer may be exposed to the heavy metal reagent by, e.g., exposing or intermixing the solid polymer with heavy metal reagent and/or by dissolving or dispersing the side chain crystallizable polymer in a solvent and intermixing with the heavy metal reagent. Other methods may also be used.

SCC polymers may contain various amounts of heavy atoms and/or crystallizable side chains, depending on the properties desired for the SCC polymer. Preferably, the content of crystallizable side chains is sufficient to substantially reduce or prevent main chain crystallization. In many cases, the amount of crystallizable side chain in the SCC polymer is in the range of about 20% to about 80% by weight, based on total polymer weight, and in some cases may be in the range of about 35% to about 65%, same basis. The length of the SCC polymer crystallizable side chain is preferably in the range of about two times to about ten times the average distance between crystallizable side chains. SCC polymers may comprise a crystalline region (e.g., formed by crystallization of the side chains below the melting point of the polymer) and a non-crystalline region (e.g., a glassy or elastomeric region formed by the non-crystallizable portions of the SCC polymer). In an embodiment, the non-crystalline region has a glass transition temperature that is higher than the body temperature of a mammal, e.g., higher than about 37° C.; in another embodiment, the non-crystalline region has a glass transition temperature that is lower than the body temperature of a mammal, e.g., lower than about 37° C. The amount of heavy atoms in a particular SCC polymer may be selected based on the degree of radiopacity and/or material (mechanical) properties desired. For example, for medical applications, a HACSCCP preferably contains from about 1% to about 90% heavy atoms, more preferably about 20% to about 50% by heavy atoms, by weight based on total weight of HACSCCP. In some cases, the SCC polymer is incorporated into a polymeric material and/or formed into a medical device as described below. When the SCC polymer is a HACSCCP, the amount of heavy atoms in the HACSCCP may be adjusted to provide the resulting polymeric material and/or medical device with the desired degree of radiopacity.

The indiscriminate incorporation of heavy atoms into side chain crystallizable polymers often disrupts or prevents otherwise crystallizable side chains from crystallizing, particularly when the levels of heavy atom incorporation are high, the side chains are relatively short, the side chains are relatively flexible, and/or the distance between side chains is relatively large. Preferably, the heavy atoms are attached to the HACSCCP in a manner that minimizes or eliminates disruption of side chain crystallinity. For example, in an embodiment, at least about 50%, preferably at least about 80%, of the heavy atoms are attached to the main chain of the HACSCCP. In another embodiment, at least about 50%, preferably at least about 80%, of the heavy atoms are attached to the ends of the side chains of the HACSCCP, e.g., to the ends of the crystallizable side chains and/or to non-crystallizable side chains. In another embodiment, at least about 50%, preferably at least about 80%, of the heavy atoms are attached to either the main chain or the side chains (crystallizable and/or non-crystallizable) of the HACSCCP. In another embodiment, the HACSCCP is a block copolymer that comprises a crystalline block and an amorphous block, and at least about 50%, preferably at least about 80%, of the heavy atoms are attached to the amorphous block.

The molecular weight of SCC polymers may be selected in view of the intended application for the polymer. For example, in some medical applications, e.g., for certain embolotherapy applications, it is desirable for the SCC polymer to flow at temperatures higher than the polymer melting point and to form a solid at temperatures below the polymer melting point. The viscosity of a molten SCC polymer generally increases as the molecular weight of the polymer increases, and thus the molecular weight of a particular SCC polymer is preferably selected to provide the desired molten polymer viscosity. For example, a suitable molecular weight range for SCC polymers used in embolotherapy products may be in the range of from about 2,000 to about 250,000, preferably from about 5,000 to about 150,000. Molecular weights are weight average as determined by high pressure size exclusion chromatography using light scattering detection.

In some cases, it may be desirable to mix or blend the SCC polymer with a second material (e.g., a second polymer) to form a polymeric material, which may then be employed in the intended application. For example, an embodiment provides a polymeric material that comprises a SCC polymer (e.g., a HACSCCP) and a second polymer. Preferably, the second polymer is biocompatible and/or bioresorbable. Examples of second polymers suitable for mixing or blending with SCC polymers to form polymeric materials include the non-inherently radiopaque polymers disclosed in U.S. Pat. No. 5,469,867 and the radiopaque polymers described in U.S. Provisional Patent Application No. 60/601,526, filed 13 Aug. 2004, both of which are incorporated by reference. Depending on the intended application, the relative amounts of SCC polymer and second polymer in the polymeric material may vary over a broad range. For example, in an embodiment, a polymeric material comprises from about 1% to about 100% of a SCC polymer and up to about 99% of a second polymer, by weight based on total. Since a polymeric material may consist solely of SCC polymer, it will be appreciated that the term "polymeric material" as used herein includes SCC polymers (such as HACSCCP's). As noted above, it will be understood that the SCC polymer itself may be a mixture or blend of two or more individual SCC polymers, each having, for example, different molecular weights, configurations and/or melting points.

A polymeric material that comprises a SCC polymer may be formed into various configurations or pre-formed shapes, e.g., a rod, a particle, or a sheet. A rod may be linear, coiled, hollow, highly elongated (e.g., a string or strand), and may have various cross-sections shapes, e.g., substantially round, substantially elliptical, substantially triangular, substantially rectangular, irregular, etc. A particle may be a spherical particle, a geometrically non-uniform particle (e.g., a flake or chip), a porous particle, a hollow particle, a solid particle, etc. A particle preferably has a excluded diameter of from about 10 microns to about 5,000 microns.

The configuration of the polymeric material may depend on various factors such as the intended application, shipping constraints, processing constraints, etc. For example, an embodiment provides a medical device that comprises a polymeric material. The polymeric material may comprise a SCC polymer. Non-limiting examples of medical devices that may comprise an SCC polymer include, for example, a stent (e.g., an expandable stent), stent graft, annuloplasty ring, vascular graft, suture, vascular cuff, septal defect repair device, heart valve, heart valve component, heart valve repair device, closure device, inducer of vasculature and connective tissue proliferation, catheter (e.g., balloon catheter configured to deliver a stent) and/or a tissue engineered implant. Various medical device embodiments are described in greater detail below. It will be appreciated that a medical device may consist solely of a polymeric material that consists solely of a SCC polymer. For example, in an embodiment, a medical device is configured to be deliverable (e.g., by injection, catheter, physical insertion, pouring, a heated rod, spraying and/or squirting) to a body cavity of a mammal. Such a device may be, for example, an embolotherapy product formed primarily of a polymeric material that comprises a HACSCCP. Thus, while certain descriptions below may be directed to medical devices, it will be understood that such descriptions also apply to polymeric materials and to SCC polymers (including HACSCCP's), unless the context indicates otherwise. Likewise, descriptions herein of polymeric materials and of SCC polymers also apply to medical devices, unless the context indicates otherwise.

A medical device that comprises a SCC polymer may be a medical device in which at least a portion of the SCC polymer is positioned at a surface of the medical device. It has been found that such positioning of the SCC polymer at a surface of the medical device allows the surface properties of the medical device to be manipulated as a function of temperature, e.g., the SCC polymer at the surface may provide increased biocompatibility and/or function as a temperature-dependent lubricant and/or adhesive, e.g., at an interface with one or more other medical devices and/or medical device components. The SCC polymer may be positioned at the surface of the medical device in various ways. For example, amounts of a SCC polymer may be applied to selected locations on the surface of the medical device; a SCC polymer may be coated onto the surface of a medical device; a film of SCC polymer may be applied to a medical device; and/or a medical device may be manufactured in such a way that a SCC polymer is formed at a surface. For example, in an embodiment, radiopaque and/or crystallizable groups may be grafted onto the surface of a polymeric medical device, e.g., by reacting radiopaque and/or crystallizable groups with functional groups on the surface and/or by polymerizing radiopaque and/or crystallizable monomers from initiation sites on the surface to thereby form polymeric radiopaque and/or crystallizable groups. Functional groups and initiation sites may be created on the surface of a polymeric medical device in various ways. For example, treatment of a polymer surface with ionizing radiation (e.g., e-beam and/or gamma radiation) and/or plasma in the presence of oxygen may result in the formation of —OH groups on the polymer surface. Such —OH groups may then be reacted with an isocyanate-functionalized radiopaque and/or crystallizable group to thereby attach those groups to the surface by forming urethane linkages. Polymerization of an appropriate monomer such as caprolactone may be initiated from the —OH groups in the presence of a suitable catalyst (such as stannous octoate) to form crystallizable PCL groups that are attached to the polymer surface. As another example, treatment of a polymer surface with ionizing radiation and/or plasma may produce active surface sites capable of initiating the polymerization of photo- and/or radiation-sensitive crystallizable monomers (1-alkenes containing from about 6 to about 30 carbons), thereby grafting a side-chain crystallizable polymer onto the surface of the polymeric medical device. The group attached to the surface may be radiopaque and/or crystallizable. In an embodiment, the polymeric medical device comprises a SCC polymer attached to the surface thereof.

The temperature-dependent properties (e.g., adhesion, lubrication, etc.) of a particular SCC polymer positioned at a surface of a medical device typically depend on the nature of the surface, the nature of the SCC polymer and the nature of the interactions between them. For example, in some cases, relatively low molecular weight SCC polymers tend to have better adhesive properties at temperatures above the melting point of the SCC polymer, as compared to the adhesive properties of those SCC polymers at temperatures below the melting point. On the other hand, in some cases, relatively high molecular weight SCC polymers tend to have better adhesive properties at temperatures below the melting point than at temperatures above the melting point. Relatively non-polar SCC polymers capable of forming relatively weak intermolecular interactions, such as heavily fluorinated SCC polymers, tend to be better lubricants than relatively polar SCC polymers capable of forming relatively strong intermolecular interactions, depending on the nature of the surface of the medical device. The use of a particular SCC polymer to provide temperature-dependent functionality at a surface of a medical device is preferably determined by routine experimentation, in view of general principles of adhesion known to those skilled in the art as informed by the guidance provided herein.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

Nucleating agents are materials that, in the presence of a polymer, make crystallization of the polymer more thermodynamically favorable. For example, a nucleating agent may accelerate polymer crystallization at a given temperature and/or induce crystallization (e.g., of a supercooled polymer) at a higher temperature than in the absence of the nucleating agent. Non-limiting examples of preferred nucleating agents include low molecular weight analogs of the SCC polymers with higher peak crystallization temperatures than the bulk polymer being crystallized, carboxylate salts (such as sodium benzoate), inorganic salts (such as barium sulfate) and various particulate materials with relatively high surface area to volume ratios.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The viscosity and/or melting point of a medical device that comprises a SCC polymer typically depends on the relative amounts of the SCC polymer and other components, if any, present in the medical device. The viscosity and/or melting point of the medical device (or polymeric material in the medical device) may be controlled by manipulating the amount of SCC polymer in the medical device and by selecting a SCC polymer that provides the resulting medical device with the desired viscosity and/or melting point. Thus, for example, to provide a polymeric material that has a melting point of 40° C., it may be desirable to select a SCC polymer that has a somewhat higher melting point, e.g., about 45° C., for incorporation into the polymeric material, to compensate for the presence of a second polymer or other component that has a tendency to lower the melting point of the SCC polymer when in admixture with it. In an embodiment, a medical device comprises a polymeric material that has a melting point in the range of about 30° C. to about 80° C.

The polymeric material of the medical device is preferably configured to flow at a temperature above the melting point. The viscosity of the polymeric material at the temperature above the melting point may vary over a broad range, depending on factors such as the intended application. For example, for embolotherapy products, the polymeric material preferably has a viscosity above the melting point that allows the medical device to be delivered to the target vasculature by a convenient technique such as by injection through a syringe and/or by flowing through a catheter. In such cases, the desired viscosity often depends on the diameter of the syringe needle or catheter, e.g., lower viscosities are typically preferred at smaller diameters. On the other hand, if the viscosity is too low, the polymeric material may migrate away from the target vasculature prior to cooling and solidifying. In an embodiment, the polymeric material of the medical device has a viscosity in the range of about 50 cP to about 500 cP at the temperature above the melting point. In another embodiment, the polymeric material has a viscosity in the range of about 500 cP to about 5,000 cP at the temperature above the melting point. In another embodiment, the polymeric material has a viscosity in the range of about 5,000 cP to about 250,000 cP at the temperature above the melting point. In another embodiment, the polymeric material has a viscosity in the range of about 250,000 cP to about 1,000,000 cP at the temperature above the melting point.

In an embodiment, the polymeric material is configured to form a solid mass upon delivery to a body cavity. The solid mass may wholly or partially conform to an interior dimension of the body cavity. For example, the polymeric material may be configured to contain an amount of an SCC polymer that provides the polymeric material with a melting point of about 40° C. The polymeric material may be further configured to be deliverable to the body cavity, e.g., the polymeric material may be in the form of a rod that may be heated to a molten state to facilitate flow. The molten polymeric material may then be delivered to a body cavity by flowing through a delivery device in the molten state. Upon arrival in the body cavity, the molten polymeric material may at least partially conform to the interior dimension of the body cavity, then cool to form a solid mass. As another example, the polymeric material may be in the form of small particles suspended in a relatively low viscosity biocompatible carrier liquid such as water or saline. The polymeric material may then be caused to flow through a delivery device to the target body cavity. The small particle of polymeric material may be heated prior to delivery, during delivery and/or within the target cavity by, thereby causing the polymeric material to flow and conform to an interior dimension of the body cavity. Upon cooling, the polymeric material may form a solid mass that continues to conform to the interior dimension of the body cavity. It will be understood that polymeric materials of various configurations and formulations before heating may vary in their ability to conform to the body cavity once warmed and may therefore be selected for this reason to tailor the treatment. Further, it will be understood that the polymeric material need not be completely melted to achieve delivery. For example, a polymeric material may be formed into a particular shape, such as a coil, then implanted into the target body cavity while retaining the preformed shape. The polymeric material (e.g., coil) may be heated prior to and/or during implantation for various reasons, e.g., to render the coil more resilient and thus easier to deliver, and/or to enable the coil to better conform to the body cavity into which it is implanted. The polymeric material may also be caused to flow outside the body then be delivered to the body cavity in a flowable state.

An embodiment provides a shape memory polymeric material that comprises a SCC polymer. For example, a SCC polymer may be configured into a first shape such as a coiled shape by a standard thermoplastic formation process and crosslinked to fix the memory of the first shape. The formed SCC polymer coil may then be heated to melt the SCC polymer, allowing it to be re-configured into a second shape such as a rod shape. The cross-linking limits or prevents thermoplastic flow while the SCC polymer is in the melted state. The SCC polymer while still in the second shape may then be cooled to a temperature at which the SCC polymer recrystallizes. The recrystallization of the SCC polymer limits or prevents the second shape (e.g., the rod shape) from returning to the first shape (e.g., the coil shape). Upon re-heating to a temperature above the melting point of the SCC polymer, the second shape returns to the first shape, e.g., the rod reverts to its memory state of a coil. Crosslinking of the SCC polymer may be carried out in various ways known to those skilled in the art.

An embodiment provides a method of treatment that comprises introducing a medical device as described herein (e.g., a medical device that comprises a SCC polymer) into a body cavity of a mammal in an amount that is effective to at least partially occlude the body cavity. In general, such a method may be used to occlude any type body cavity including, e.g., various body cavities that may commonly be referred to as tubes, tubules, ducts, channels, foramens, vessels, voids, and canals. In a preferred embodiment, the medical device is an embolotherapy product. Preferably, the SCC polymer is a HACSCCP. In another preferred embodiment, the body cavity comprises vasculature, e.g., an arteriovenous malformation or a blood vessel such as a varicose vein. The medical device may be introduced to the body cavity in a variety of ways, including by injection, by catheter and by surgical implantation. For a particular body cavity, the medical device is preferably selected so that the polymeric material has a melting point that is sufficiently high that the polymer forms a solid mass at the normal temperature of the body cavity, and sufficiently low so that that softened or molten polymeric material may conform to a dimension of the body cavity with little or no thermal damage to the mammal into which it is introduced. Introduction of such a polymeric material into the body cavity thus may comprise heating the polymeric material to a temperature that is higher than the melting point and/or cooling it to a temperature that is lower than the melting point.

Various types of delivery devices may be used to introduce the medical device to the body cavity, e.g., plastic tubes, catheters, fine cannula, tapered cannula and various types of syringes and hypodermic needles which are generally known to and available to those in the medical profession. An embodiment provides a medical apparatus that comprises a polymeric material and a delivery device, where the polymeric material is an SCC polymer, and where the polymeric material and the delivery device are mutually configured to facilitate delivery of the polymeric material to a body cavity by the delivery device. The polymeric material is preferably contained within the delivery device, in an amount that may vary somewhat depending on the particular body cavity to be occluded and the amount and type of occlusion desired. Those skilled in the art will be aware of the size of the cavity being occluded based on the size of the patient, general knowledge of anatomy, and thus use of diagnostic methods such as X-ray and MRI. Those skilled in the art will be able to determine the amount of polymer material to be included within the delivery device. In general, an excess amount of polymeric material should be included in the delivery device in order to provide for a certain margin of error. In an embodiment, the medical apparatus comprises an embolotherapy product and a tube, where the embolotherapy product comprises a SCC polymer as described herein and where the tube is configured to facilitate flow of the embolotherapy product to a body cavity. For example, the tube may comprise a needle, cannula, syringe, and/or catheter, and may be equipped with a heater configured to heat the embolotherapy product to a temperature above its melting point, e.g., to a temperature in the range of about 30° C. to about 80° C. The polymeric material may be included within the delivery device in a solid form or heated separately and provided in the delivery device in a flowable form. In one embodiment, the medical apparatus may be prepackaged with the polymeric material present within the delivery device and may thereafter be heated in order to make the polymeric material flowable. Heating may be applied from an exterior source such as an air, water or oil bath or an electrical heater, in which case both the delivery device and the polymeric material may be heated. Heating can also be applied from an interior source, e.g., using a small electrical resistive element at the end of a catheter through which a thin rod of the solid polymeric material is passed, or using a small laser directed at the tip of a rod of polymeric material emerging from the end of a catheter.

The delivery device may include an extrusion nozzle which is preferably relatively small in diameter such that it will not seriously damage the tissue in the vicinity of the body cavity to be occluded, but sufficiently large such that the polymeric material can be readily extruded from the nozzle. For example, in application that involves the occlusion of a body channel, the size of the nozzle is generally related to the inside diameter of the channel into which it is placed. For example, a 24 gauge needle typically fits within the opening of the punctum which leads to the canaliculus. A 2 mm catheter is typically appropriate for introducing the polymeric material into the fallopian tubes. A ¼ inch cannula is preferred for introducing the polymeric material into the inner cavity of an adult humerus. When delivered in the molten state, the polymeric material is preferably selected to have a viscosity that facilitates passage of the polymeric material through the extrusion nozzle. In general, relatively lower viscosities are preferred for relatively smaller diameter nozzles.

It will be understood that the delivery device may include an extrusion nozzle with one or more delivery ports. The polymeric material may be dispensed through multiple ports serially or simultaneously. This approach may accommodate better packing and/or stabilization of the polymeric material that cools and it may allow for delivery of more polymeric material across a large surface area. That various configurations and formulations may be simultaneously delivered by the use of various delivery ports.

For example, in an embodiment, two or more polymeric materials (each comprising a SCC polymer) may be delivered sequentially to a body cavity. In an embolotherapy embodiment, a first polymeric material is delivered to vascular structure. The first polymeric material may have a first configuration, such as a coil. The coil may be preformed, e.g., a shape memory coil as described above that is delivered in a rod shape (forming a coil upon delivery), or may be a coil that is formed during delivery by extruding the polymeric material through a delivery port of the delivery device having an appropriately configured die. The first polymeric material is preferably delivered at a temperature higher than its melting point, e.g., higher than the melting point of a first SCC polymer in the first polymeric material.

A coil may be a relatively open structure that partially occludes the vascular structure, reducing the blood flow without completely stopping it. Although such partial occlusion may be appropriate in some cases, in other cases further occlusion may be desired. Such further occlusion may be accomplished by delivering a second polymeric to the vascular structure in operable proximity to the first polymeric material. The second polymeric material is preferably delivered at a temperature higher than the its melting point, e.g., higher than the melting point of a second SCC polymer in the second polymeric material. The second polymeric material preferably has a lower viscosity than the first polymeric material, such that it may at least partially fill interstices or gaps in the first polymeric material and/or between the first polymeric material and the interior of the vascular structure. Thus, for example, the second polymeric material may have the consistency of a paste at a temperature above its melting point during delivery, allowing it to fill in the spaces of the first polymeric material coil.

One or more additional polymeric materials may be delivered to a location in operable proximity to the first and second polymeric materials. For example, the first and second polymeric materials may only partially occlude the vascular structure, although typically to a greater extend than the first polymer alone. In such a case, it may be desirable to deliver a third polymeric material to provide further occlusion. The third polymeric material is preferably delivered at a temperature higher than its melting point, e.g., higher than the melting point of a third SCC polymer in the third polymeric material. The third polymeric material preferably has a lower viscosity than the first polymeric material, and more preferably lower than the second polymeric material, such that it may at least partially fill interstices or gaps in the polymeric mass formed by the first and second polymeric materials and/or between the mass and the interior of the vascular structure.

Those skilled in the art will appreciate that multiple variations of the embodiments described above may be practiced. For example, a single polymeric material may be delivered in multiple doses or in different forms, e.g., as a coil in a first delivery and as a paste in a second delivery, or as a paste in both the first and second deliveries. Two or more polymeric materials may be delivered simultaneously, e.g., a first polymeric material in a coil shape may be coated or mixed with a second polymeric material in a paste or liquid form to form a composite that comprises both polymers, and the resulting composite may then be delivered to the body cavity. Various body cavities may be the target of the delivery, and/or the order in which the various polymeric materials and forms are delivered may be varied. Delivery of a polymeric material that comprises a SCC polymer may be combined, sequentially or simultaneously, with the delivery of a different material, e.g., a metal embolic coil. Thus, for example, a polymeric material may be delivered to a body cavity, and a metal embolic coil may be delivered to the body cavity in contact with the polymeric material. Various periods of time may pass between deliveries, e.g., a polymeric material coil may be delivered to provide partial occlusion of a body cavity, and a second polymeric material paste may be delivered to a location in operable proximity to the coil minutes, hours, days, weeks, months, or years later.

For embodiments in which the polymeric material is delivered in the molten state, once a polymeric material has been included within the delivery device and heated to a flowable state, the nozzle of the delivery device (e.g., such as the tip of a needle, catheter, and/or squirt nozzle) may be inserted into an opening of a channel (or through the wall of cavity) to be occluded and the polymer may be dispensed out of the nozzle into the body cavity. The injection is preferably continued until the desired amount of occlusion (e.g., vasculature blockage) is obtained. In some instances, it may be desirable to occlude only part of a cavity. Thereafter, the nozzle of the delivery device may be withdrawn.

After the polymeric material has been delivered, the method may continue without operator interaction. For example, in the case of embolotherapy, the circulatory system of the mammal will typically cause a cooling effect on the surrounding tissues which will cool the injected polymeric material. The polymeric material is preferably selected such that it cools and solidifies after losing only a small amount of energy, i.e., hardens after decreasing in temperature by only a few degrees centigrade. Usually, cooling takes only a few seconds or minutes to occur, although there are times when it may be desirable for cooling to occur more slowly, e.g., in the case where a bone is reset after delivery. After cooling has taken place, the polymer preferably solidifies within the cavity in a manner conforming to the shape of the cavity and the channel is at least partially filled or blocked. The polymeric material may remain in place in the cavity over long periods of time. For preferred medical devices comprising biocompatible, non-immunogenic material, little or no adverse reaction is obtained. In certain embodiment, the polymer is bioresorbable, and thus may diminish over time, in which case surrounding tissue may fill the previously occluded region.

An effective cavity occlusion may also be achieved through the use of SCC polymer material and various excipients. For instance, the SCC polymer material may be delivered with (1) a photopolymerizable material that cross links through the use of a light; (2) a blood reactive substance that stimulates clotting such as collagen or thrombin, and/or (3) a nucleating agent.

In an embodiment, the polymeric material may be readily removed so as to again provide a cavity which functions in a normal manner. For example, it may be desirable to remove the polymeric material from a vas deferens or fallopian tube to restore fertility. The polymeric material may be removed in various ways. For example, the polymeric material may be removed by simple mechanical extraction. In certain instances, devices such as forceps and/or catheters with various attachment prongs connected thereto can be inserted into the channel and used to attach to the polymeric material and pull the polymeric material out of the cavity or force it forward into a second cavity so that the first cavity is no longer occluded and the polymeric material will not cause any damage. Alternatively, a device such as a heated wire may be brought into contact with the solidified polymeric material. By heating the polymeric material with the heated wire, the temperature of the polymeric material is raised above the melting point of the polymeric material so that it again becomes flowable. In the case of a channel (such as a duct or vein), the heating may be continued until the flowable polymeric material flows from the channel and the channel is reopened to provide normal function. In certain circumstances, the liquid plug can be drawn, aspirated or forced out of a channel, e.g., by suction with a gentle vacuum or by using mild pressure created by air or a saline flow and/or by mechanical breakup along with trapping and aspiration.

A preferred method of removing the solidified polymeric material from a channel or other cavity is to inject a lipophilic material such as a naturally occurring oil or a fatty acid ester into the channel in the area surrounding the solidified polymeric material. Preferably, a lipophilic material is selected that has a tendency to diffuse into the polymeric material, thereby reducing its melting point. The lipophilic material is preferably added in an amount that is effective to reduce the melting point of the polymeric material below body temperature to such an extent that the polymer becomes flowable. Once the polymer becomes flowable, the natural mechanical movement that occurs within channels of living beings will tend to move the polymer from the channel, thereby restoring the normal function of the channel.

In a preferred embodiment, the medical device comprises a stent. The stent may comprise various configurations, e.g., a configuration selected from the group consisting of a sheet stent, a braided stent, a self-expanding stent, a wire stent, a deformable stent, and a slide-and-lock stent.

In a preferred embodiment, the stent comprises at least two substantially non-deforming elements arranged to form a tubular member, the non-deforming elements being slidably interconnected for allowing the tubular member to expand from a collapsed diameter to an expanded diameter. In another variation the tubular member comprises a series of slideably engaged radial elements and at least one locking mechanism which permits one-way sliding of the radial elements from a first collapsed diameter to a second expanded diameter.

A stent on a catheter is commonly collectively referred to as a stent system. Catheters include but are not limited to over-the-wire catheters, coaxial rapid-exchange designs and the Medtronic Zipper Technology that is a relatively new multi-exchange delivery platform. Such catheters may include, for instance, those described in U.S. Pat. Nos. 4,762,129; 5,232,445; 4,748,982; 5,496,346; 5,626,600; 5,040,548; 5,061,273; 5,350,395; 5,451,233 and 5,749,888. Additional examples of suitable catheter designs include those described in U.S. Pat. Nos. 4,762,129; 5,092,877; 5,108,416; 5,197,978; 5,232,445; 5,300,085; 5,445,646; 5,496,275; 5,545,135; 5,545,138; 5,549,556; 5,755,708; 5,769,868; 5,800,393; 5,836,965; 5,989,280; 6,019,785; 6,036,715; 5,242,399; 5,158,548; and 6,007,545. The disclosures of the above-cited patents are incorporated herein in their entirety by reference thereto.

Catheters may be specialized for various purposes such as to produce an ultrasound effect, electric field, magnetic field, light and/or temperature effect. Heating catheters may include for example those described in U.S. Pat. Nos. 5,151,100, 5,230,349; 6,447,508; and 6,562,021 as well as WO 90\14046 A1. Infrared light emitting catheters may include for example those described in U.S. Pat. Nos. 5,910,816 and 5,423,321. The disclosures of the above-cited patents and patent publications are incorporated herein in their entirety by reference thereto.

In another preferred variation, the stent further comprises an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metalloproteinase, and lipid lowering, cholesterol modifying, antithrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

A preferred SCC polymer for use in the fabrication of a stent should fulfill at least some of the following criteria:

- Radiopacity is preferably sufficient to ensure visibility of the stent structure against the background of a human chest by X-ray fluoroscopy, the standard method used in the clinic.
- Stents according to aspects of the present invention are preferably formed with walls for providing a low crossing profile and for allowing excellent longitudinal flexibility. In preferred embodiments, the wall thickness is about 0.0001 inches to about 0.0250 inches, and more preferably about 0.0010 to about 0.0100 inches. However, the wall thickness depends, at least in part, on the selected material. For example, the thickness may be less than about 0.0060 inches for plastic and degradable materials and may be less than about 0.0020 inches for metal materials. More particularly, for a 3.00 mm stent application, when a plastic material is used, the thickness is preferably in the range of about 0.0040 inches to about 0.0045 inches. However, a stent having various diameters may employ different thicknesses for biliary and other peripheral vascular applications. The above thickness ranges have been found to provide preferred characteristics through all aspects of the device including assembly and deployment. However, it will be appreciated that the above thickness ranges should not be limiting with respect to the scope of the invention and that the teachings of the present invention may be applied to devices having dimensions not discussed herein.
- The stents are preferably hemocompatible to prevent acute thrombosis. Accordingly, the device surfaces are preferably resistant to protein adsorption and platelet/monocyte attachment. Further, the device surfaces ideally favor endothelial overgrowth but discourage attachment and growth of smooth muscle cells (which are responsible for the occurrence of restenosis).
- Stents preferably maintain their mechanical strength (e.g., hoop strength) for a period of about 1-24 months, more preferably about 3-18 months, more preferably still about 3-12 months, and most preferably about 3-6 months.
- Stents preferably have a desirable biodegradation and bioresorption profile such that the stents reside for a period of time in the body lumen such that at a later time any stent, bioresorbable or metal or other, may be used to re-treat the approximate same region of the blood vessel or allow for other forms of vessel re-intervention such as vessel bypass.

In an embodiment, an SCC polymer-containing medical device comprises a stent and/or a catheter, and thus an SCC polymer-containing medical device may be a stent, or a stent system comprising a stent and a delivery catheter. The SCC polymer may be incorporated into such a medical device in various ways. For example, in various embodiments, the body of the stent and/or catheter may comprise or consist essentially of a SCC polymer; the stent and/or catheter may be coated with a SCC polymer; the SCC polymer may be located at an interface between parts of the medical device, e.g., a between a stent and a catheter; the SCC polymer may be a HACSCCP; and/or the SCC polymer may be positioned at a surface of the stent and/or catheter. In medical device embodiments, the SCC polymer is preferably biocompatible, and preferably has a melting point in the in the range of about 30° C. to about 80° C.

A stent comprising a SCC polymer may be of any design (e.g., slide-and-lock stents, sheet stents (sometimes referred to as jelly-roll stents), deformable stents, and self-expanding stents) suitable for a given application. Preferably, a stent comprising an SCC polymer is designed to be readily implantable in the artery or tissue of an animal, such as a human, and to be expandable and/or suitable for holding open an artery, e.g., after said artery is opened via a medical procedure, such as an angioplasty. Examples of suitable stent designs for use in the present invention include "slide-and-lock" stents, including those disclosed in U.S. Pat. Nos. 6,033,436; 6,224,626 and 6,623,521, co-pending U.S. patent application Ser. No. 11/016,269, filed Dec. 17, 2004, and co-pending U.S. patent application Ser. No. 11/200,656, filed Aug. 10, 2005, all of which are incorporated herein by reference.

With reference now to FIG. 1, a portion of a preferred stent embodiment 320 is illustrated wherein radial elements 320(1), 320(2) are slidably interconnected. Each radial element is provided with a rail 328 having a plurality of deflectable teeth 326. Each of the teeth is angled upward and is configured to deflect downward (i.e., in a radial direction). As the locking tabs 322, 324 slide along the deflectable teeth 326, the teeth are caused to deflect downward for allowing the tabs 322, 324 to pass over the teeth 326 during deployment. However, due to the angle of the teeth, the locking tabs may only move in one direction. More particularly, if a compressive force pushes the radial elements 320(1), 320(2) back toward the collapsed condition, the locking tabs 322, 324 will abut against the teeth 326, thereby preventing further relative movement. All or some of the various elements (e.g., the elements 320(1), 320(2), 322, 324, 326, 328) of the stent embodiment 320 may comprise or consist essentially of a SCC polymer.

Other suitable stent designs adaptable for use herein include those used traditionally in metal and polymeric stents, including various mesh, jelly-roll, sheet, zigzag, and helical coil designs, e.g., the deformable stents by Palmaz such as U.S. Pat. No. 4,733,665 and its successors which have controllable expansion and a portion of the prosthesis that deforms with a force in excess of the elastic limit. Other stent designs include the following designs and their successors: U.S. Pat. No. 5,344,426 by Lau, U.S. Pat. Nos. 5,549,662 and 5,733,328 by Fordenbacher, U.S. Pat. Nos. 5,735,872 and 5,876,419 by Carpenter, U.S. Pat. No. 5,741,293 by Wijay, U.S. Pat. No. 5,984,963 by Ryan, U.S. Pat. Nos. 5,441,515 and 5,618,299 by Khosravi, U.S. Pat. Nos. 5,059,211; 5,306,286 and 5,527,337 by Stack, U.S. Pat. No. 5,443,500 by Sigwart, U.S. Pat. No. 5,449,382 by Dayton, U.S. Pat. No. 6,409,752 by Boatman, and the like.

Various temperature-dependent properties of the SCC polymer (e.g., strength, flexibility, crystallinity, adhesion, etc.) may be manipulated to enhance the performance of the medical device. For example, the stent may be an expandable stent, e.g., a stent that is designed or configured to have a changeable cross-sectional dimension, e.g., a cross-sectional dimension that may be increased upon positioning of the stent within a blood vessel where expansion is desired. The stent may be mechanically expandable, heat expandable, or it may be a hybrid stent that is both mechanically and thermally expandable. In an embodiment, the body of the expandable stent comprises an amount of SCC polymer that is effective to allow the stent to be expandable at a temperature above a melting point of the SCC polymer. For example, the expandable stent may be positioned within the blood vessel, expanded at a temperature above a melting point of the biocompatible inherently radiopaque side chain crystallizable polymer, then cooled (actively or passively) to a temperature below the melting point. In an embodiment, at least a portion of the expandable stent is heat expandable. Preferably, the heat expandable portion is expandable at a temperature above a melting point of the side chain crystallizable polymer. In an embodiment, the expandable stent or a portion thereof comprises an amount of SCC polymer that is effective to allow the stent to be expandable at a temperature that is above body temperature (about 38° C.). For example, the stent may consist essentially of an SCC polymer having a melting point in the range of about 40° C. to about 80° C. Heating such a stent to a temperature above the melting temperature increases the flexibility of the stent, allowing it to assume the size and shape desired for adequate function, e.g., support of the blood vessel. In an embodiment, Prior to, during and/or after appropriate positioning within the blood vessel, the expandable stent may be heated to a temperature above the melting point and expanded by, e.g., use of a balloon catheter positioned within the stent, in a manner generally known to those skilled in the art. Optionally, a heated liquid may be circulated through the balloon catheter to provide heating to the expandable stent. After expansion, the stent may be cooled, e.g., by allowing it to cool to the temperature of the surrounding blood and/or tissue, and/or by circulating a cooling liquid through the balloon catheter. Upon cooling below the recrystallization temperature of the SCC polymer (which may be different from or the same as the melting temperature), the stent becomes much more rigid and thus capable of providing the desired function, e.g., support of the blood vessel. The amount and type of SCC polymer in the stent may be selected based on the temperature-dependent flexibility properties desired for the stent, as determined by routine experimentation.

In an embodiment, the medical device (comprising a SCC polymer) is a catheter, e.g., a device having any of the catheter designs described above. The SCC polymer may be incorporated into such a catheter in various ways, as discussed above. In an embodiment, at least a portion of the SCC polymer is positioned at a surface of the catheter. It has been found that such positioning of the SCC polymer at a surface of the catheter allows the surface properties of the catheter to be manipulated as a function of temperature, e.g., the SCC polymer may function as a temperature-dependent lubricant and/or adhesive as discussed above.

In an embodiment, the medical device (comprising a SCC polymer) is a stent system comprising a stent and a catheter. The SCC polymer may be incorporated into such a stent system in various ways, e.g., in the body or at a surface of the stent, in the body or at a surface of the catheter, and/or at an interface between the stent and the catheter. The SCC polymer may be positioned at an interface between two medical devices in various ways. For example, amounts of a SCC polymer may be applied to selected locations on the surface of one or both of the stent and catheter; a SCC polymer may be coated onto one or both of the surfaces of the stent and catheter; a film of SCC polymer may be applied to one or both of the surfaces of the stent and catheter; and/or a one or both of the surfaces of the stent and catheter may be manufactured in such a way that a SCC polymer is formed at the surface(s). Methods for positioning a SCC polymer at a surface and/or interface are described above.

In an embodiment, the SCC polymer is configured to provide temperature-dependent adhesion between the stent and the catheter. For example, as discussed above, a SCC polymer may be selected to provide greater adhesion at temperatures above the melting point of the SCC polymer. Such a SCC polymer may be provided at an interface between the stent and the catheter and heated to temperature above the melting point, thus increasing the amount of adhesion between the stent and the catheter. The stent may then be positioned at the desired site within the vascular system. During such positioning, the adhesive properties of the SCC polymer desirably reduce or prevent slippage between the stent and catheter. After expansion of the stent, the SCC polymer may be allowed to cool (and/or actively cooled by circulating a liquid through the catheter) to a temperature below the melting point of the SCC polymer. Upon such cooling, the adhesive character of the SCC polymer is reduced, allowing the catheter to be cleanly withdrawn from the vicinity of the stent without undesirable re-positioning of the stent. In other embodiments, the SCC polymer is selected to provide greater adhesion at temperatures below the melting point of the SCC polymer. In such embodiments, the stent is preferably positioned at a temperature below the melting point of the SCC polymer, while adhesion is greater (for the SCC polymer of this embodiment), expanded to the desired diameter within the vasculature, then heated to reduce the adhesion between the stent and catheter, thereby facilitating detachment and withdrawal of the catheter while minimizing undesirable re-positioning of the stent. Thus, in some embodiments, the SCC polymer is heated to increase adhesion and/or cooled to decrease adhesion; in other embodiments the SCC polymer is cooled to increase adhesion and/or heated to decrease adhesion. Preferably, the SCC polymer is a HACSCCP.

In another embodiment, a medical device is formed in vivo by introducing a polymeric material into a body cavity, then forming a channel through the polymeric material. For example, a stent may be formed by introducing a polymeric material (containing a SCC polymer) into a blood vessel in a manner similar to that described above for embolization, then forming a channel through the polymeric material. Preferably, the SCC polymer is a HACSCCP. The channel is preferably substantially coaxial to the blood vessel, thus allowing blood to flow through the channel. The channel may be formed in various ways. For example, in one embodiment, the polymeric material is formed around a cylindrical mold. The SCC polymer in the polymeric material is selected so that the adhesion between the mold and the polymeric material is greater at temperatures below the melting point of the SCC polymer. The mold and polymeric material are then inserted into the vasculature and positioned to at least partially occlude a blood vessel. The mold is then heated to a temperature slightly above the melting point of the polymeric material, thereby reducing adhesion between the polymeric material and the mold. The mold is then withdrawn, leaving behind a cylindrical hole in the polymeric material. Withdrawal of the mold without undesirable repositioning of the polymeric material is facilitated by the temperature-dependent adhesive properties of the SCC polymer. Other methods may also be used to form channels in polymeric materials, e.g., other mold shapes and configurations and/or by heating a portion of the polymeric material to a temperature above the melting point of the SCC polymer or polymeric material. The size, shape, number and configuration of the channels may be controlled in various ways. For example, heat energy may be applied at various levels and in various forms, e.g., by laser and/or by inserting heated implements (such as a heated wire) into the polymeric material.

EXAMPLE 1

To a resin flask equipped with a thermometer, stirrer and reflux condenser is added 500 grams (g) of octamethylcyclotetrasiloxane, 250 g of octaphenylcyclotetrasiloxane, and 250 g of octa(iodophenyl)cyclotetrasiloxane, a heavy atom bearing monomer. The flask and contents are heated to 150° C. and 0.11 g of potassium hydroxide-isopropanol complex (neutral equivalent=193.5) is added (Si:K ratio about 4470: 1). The solution is allowed to stir for approximately 30 minutes. Once the solution becomes too viscous to stir effectively (due to polymer formation), the polymer is heated to approximately 165° C. for 3 to 4 hours, then cooled to room temperature. The resulting polymer is a HACSCCP comprising recurring units of the formula (IV) in which $A^3$ and $A^4$ are iodinated phenyl groups, recurring units of the formula (V) in which $R^{10}$ and $R^{11}$ are phenyl groups, and dimethylsiloxane recurring units.

EXAMPLE 2

To a resin flask equipped with a thermometer, stirrer, reflux condenser and 250 g of xylene stirred at approximately 135° C., a solution of 20 g of 4-iodo styrene, 60 g of docosanyl acrylate, and 11 g of di-tert-butyl peroxide is added over a period of approximately 3 hours. After addition is complete, the mixture is allowed to continue stirring for approximately another 3 hours to affect a more complete conversion, then cooled to room temperature. The resulting polymer is a HACSCCP comprising recurring units of the formula (II) in which $R^7$ and $R^8$ are H, $A^3$ is $C_6H_4$—I, and recurring units of the formula (III) in which $L^3$ is an ester linkage and $R^9$ comprises a $C_{22}$ hydrocarbon group.

EXAMPLE 3

To a 500 mL 2-necked round-bottom flask equipped with a mechanical stirrer and a rubber septum, 30 g of a monomer of the formula (VII) (I2DT-docosanyl) and 240 ml of methylene chloride are added. The solids are dissolved with stirring. About 4.34 g of triphosgene dissolved in 30 mL of methylene chloride is placed in a airtight syringe and added to the reaction flask with a syringe pump at a constant rate over a period of about 2 to 3 hours. The resulting viscous polymer solution is diluted by adding about 150 mL of tetrahydrofuran and 10 mL of water. The polymer is isolated by precipitating the polymer solution in isopropanol, filtering the resulting solid and drying under vacuum. The polymer is a HACSCCP comprising a recurring unit of the formula (I) in which $X^1$ is I, $y^1$ is 2, $y^2$ is zero, $A^1$ is —(C=O)—, $R^5$ is —$CH_2CH_2$—, $R^6$ is —$CH_2$—, and Q is a crystallizable ester group containing 23 carbons.

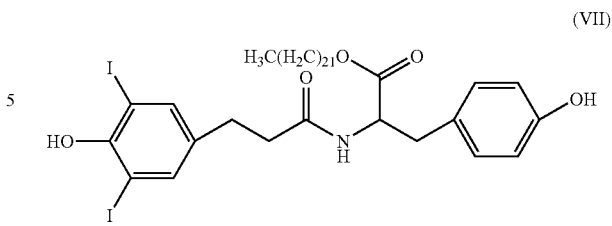

(VII)

EXAMPLE 4

An embolization is carried out as follows: A HACSCCP prepared as described in Example 3 is formed into a rod-shaped embolic medical device and loaded into a heated catheter. A physician delivers the catheter to a Arteriovenous Fistula (AVF) to be embolized. A baseline angiogram is performed with fluoroscopy to better determine the region to be embolized. The rod of HACSCCP embolic agent is pushed through the catheter to the target site. Localized heating in the catheter melts the HACSCCP, allowing it to flow through the catheter and to the target site in an liquid form that conforms to the AVF and embolizes the tissue. The HACSCCP cools and recrystallizes at the target site. Delivery of the HACSCCP is continued until blood flow ceases in the target area. Blood flow cessation is confirmed by injecting contrast agent and viewing by fluoroscopy. The HACSCCP is visible under fluoroscopy. The catheter is cooled to stop the flow of unneeded HACSCCP. The catheter is withdrawn.

EXAMPLE 5

An embolization is carried out as described in Example 4, except that a higher viscosity HACSCCP is utilized and the HACSCCP is delivered to an artery for the treatment of an aneurysm. Embolization is achieved.

EXAMPLE 6

Embolization of a traumatic bleeding artery is carried out as generally described in Example 4, except that, prior to delivery, the HACSCCP is formed into the shape of a coil and crosslinked by irradiation, thereby forming a memory coil. During heating, the memory coil softens and forms a flexible rod that is delivered to the artery through the catheter. Upon delivery, the flexible rod cools and resumes a coil shape within the artery, thereby reducing the blood flow.

EXAMPLE 7

Into a one-liter reactor is charged 90 grams of iodostyrene and 10 grams of hydroxy ethyl methacrylate (HEMA). About 200 ml of the toluene (solvent) is added and the reactor is carefully purged with argon. Then 0.5 mol percent of azobisisobutyronitrile (AIBN, polymerization initiator) is added and the reaction is brought to 70 degrees C. for about 24 hours. The composition of the resulting copolymer of iodotyrene and HEMA is confirmed by nuclear magnetic resonance (NMR) spectroscopy. Then, 30 grams of caprolactone is added. To azeotropically dehydrate the reaction system, about 10% of the toluene is removed by distillation, and then 100 parts per million of stannous octoate catalyst is added. The temperature is raised to 100° C. and the caprolactone is polymerized by grafting off the pendant hydroxyl groups of the iodostyrene/HEMA copolymer. The resulting HACSCCP is coagulated in alcohol and dried. The HACSCCP contains about 23% (NMR) semicrystalline polycaprolactone (PCL) in the form of crystallizable PCL side chains. The intrinsic viscosity of the HACSCCP is greater than 1.0 in toluene at 30° C., indicating a relatively high molecular weight.

EXAMPLE 8

A series of HACSCCP materials are prepared in a manner similar to that described in Example 7, except that the relative amounts of HEMA and iodostyrene are varied, along with the molecular weights of the backbone and PCL side chains. The series of HACSCCP polymers exhibits a range of melting points, depending on the length and spacing between the PCL crystallizable side chains (longer lengths and/or closer spacing resulting in higher melting points, e.g., up to about 60° C.). The series of HACSCCP polymers also exhibits a range of radiopacities, depending on the number of iodostyrene recurring units incorporated into the HACSCCP.

It will be appreciated by those skilled in the art that various omissions, additions and modifications may be made to the materials and methods described above without departing from the scope of the invention, and all such modifications and changes are intended to fall within the scope of the invention, as defined by the appended claims.

What is claimed is:

1. A medical device comprising a polymer, wherein the polymer comprises:
a main chain;
a plurality of crystallizable side chains; and
a plurality of heavy atoms attached to the polymer, the heavy atoms being present in an amount that is effective to render the polymer radiopaque;
wherein the polymer comprises a recurring unit of the formula (VI):

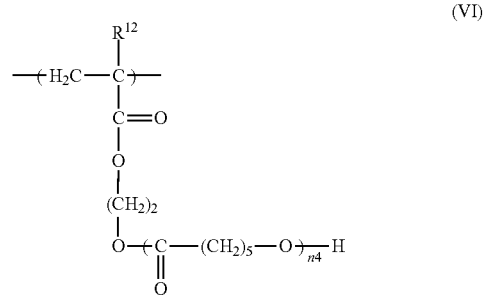

wherein $R^{12}$ is H or $CH_3$ and n4 is an integer in the range of about 1 to about 1,000.

* * * * *

UNITED STATES PATENT AND TRADEMARK OFFICE
CERTIFICATE OF CORRECTION

PATENT NO. : 8,703,113 B2
APPLICATION NO. : 11/335771
DATED : April 22, 2014
INVENTOR(S) : Brandom et al.

It is certified that error appears in the above-identified patent and that said Letters Patent is hereby corrected as shown below:

On the Title Page, References Cited

In column 2 (page 1, item 56) line 26, Under Other Publications, change "prosthesesBiomaterials" to --prosthesis Biomaterials--.

In column 1 (page 2, item 56) line 4, Under Other Publications, change "1O3" to --103--.

In column 1 (page 2, item 56) line 25, Under Other Publications, change "form" to --from--.

In column 1 (page 2, item 56) line 41, Under Other Publications, change "n-Octadeeyl" to --n-Octadecyl--.

In column 2 (page 2, item 56) line 22, Under Other Publications, change "Fluroalkyl" to --Fluoroalkyl--.

In column 2 (page 2, item 56) line 31, Under Other Publications, change "Poly(di-*n*-heptylsaline)," to --Poly(di-*n*-heptylsilane),--.

In the Specification

Column 1 line 59, Change "cyrstallizable" to --crystallizable--.

Column 2 line 2, Change "crstallizable" to --crystallizable--.

Column 2 line 33, Change "with" to --which--.

Column 4 [Structure (I)] lines 57-62,

Change " 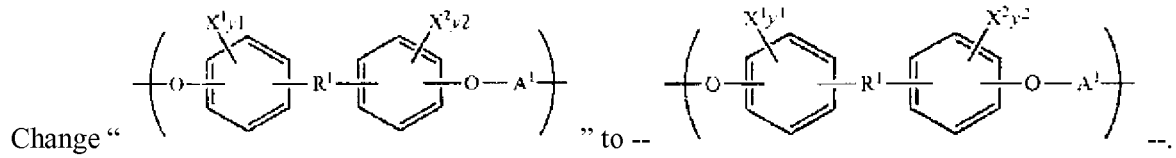 --.

Signed and Sealed this
Seventh Day of October, 2014

Michelle K. Lee
*Deputy Director of the United States Patent and Trademark Office*

CERTIFICATE OF CORRECTION (continued)
U.S. Pat. No. 8,703,113 B2

Column 5 lines 15-20,

Change " 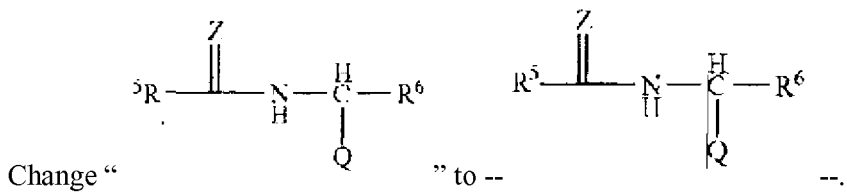 " to -- --.

Column 5 lines 15-20,

Change " 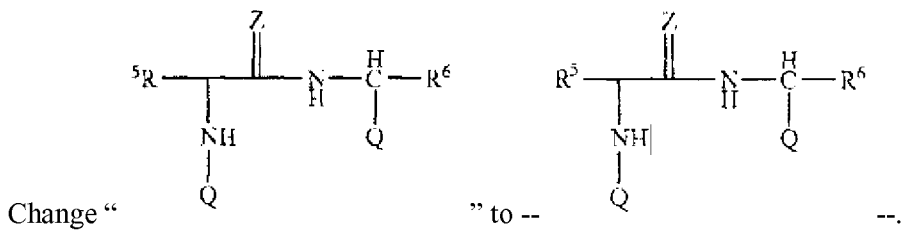 " to -- --.

Column 6 [Structure (Ia)] lines 9-12,

Change " 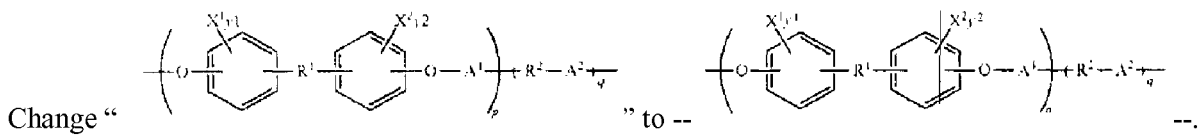 " to -- --.

Column 6 line 16, Change "$X^{\underline{1}}$" to --$X^1$--.

Column 8 line 66, Change "know" to --known--.

Column 9 line 37, Change "Sci," to --Sci.--.

Column 13 lines 39-40, Change "dioxorubicin," to --doxorubicin,--.

Column 13 line 43, Change "Rofexcoxib," to --Rofecoxib,--.

Column 16 line 6, Change "that that" to --that--.

Column 25 lines 12-13, Change "atom bearing" to --atom-bearing--.

Column 26 lines 59-60, Change "iodotyrene" to --iodostyrene--.